(12) United States Patent
Schuler et al.

(10) Patent No.: US 12,708,431 B2
(45) Date of Patent: Aug. 18, 2026

(54) TUBULAR LARGE BORE TRANSSEPTAL CROSSING SHEATH

(71) Applicant: CIRCA SCIENTIFIC, INC., Englewood, CO (US)

(72) Inventors: Brian Schuler, York, PA (US); Steve Howard, La Jolla, CA (US); Brad Klos, Solana Beach, CA (US)

(73) Assignee: Circa Scientific, Inc., Englewood, CO (US)

( * ) Notice: Subject to any disclaimer, the term of this patent is extended or adjusted under 35 U.S.C. 154(b) by 216 days.

(21) Appl. No.: 16/896,604

(22) Filed: Jun. 9, 2020

(65) Prior Publication Data

US 2021/0353356 A1 Nov. 18, 2021

Related U.S. Application Data

(60) Provisional application No. 63/024,986, filed on May 14, 2020.

(51) Int. Cl.

*A61B 18/14* (2006.01)
*A61B 18/12* (2006.01)
*A61B 18/00* (2006.01)

(52) U.S. Cl.

CPC ...... *A61B 18/1487* (2013.01); *A61B 18/1206* (2013.01); *A61B 18/1492* (2013.01);

(Continued)

(58) Field of Classification Search

CPC ............ A61B 18/1487; A61B 18/1206; A61B 18/1492; A61B 2018/00077;

(Continued)

(56) References Cited

U.S. PATENT DOCUMENTS 2,056,377 A 10/1936 Wappler
4,483,338 A 11/1984 Bloom et al.

(Continued)

FOREIGN PATENT DOCUMENTS

CN 2291901 9/1998
CN 105193476 12/2015

(Continued)

OTHER PUBLICATIONS

U.S. Appl. No. 16/896,582, filed Jun. 9, 2020, Transseptal Crossing System For Single Pass Large Bore Access.

(Continued)

*Primary Examiner* — Khadijeh A Vahdat
(74) *Attorney, Agent, or Firm* — Bochner PLLC; Andrew D. Bochner; Ross Brown

(57) ABSTRACT

Disclosed is an electrically enabled introducer sheath, such as for crossing a septum into a left atrium and guiding a large bore catheter across the septum and into the left atrium. The sheath includes an elongate, flexible tubular body, having a proximal end, a distal end and an electrically conductive sidewall defining a central lumen. A tubular insulation layer surrounds the sidewall and leaves exposed an annular conductive surface at the distal end. The tubular body has a proximal hub, having at least one access port in communication with the central lumen and a connector in electrical communication with the conductive sidewall. The central lumen is configured to receive a radio frequency conducting wire, to facilitate crossing the septum.

15 Claims, 9 Drawing Sheets

(52) U.S. Cl.
CPC ............... *A61B 2018/00077* (2013.01); *A61B 2018/00083* (2013.01); *A61B 2018/00178* (2013.01); *A61B 2018/00351* (2013.01); *A61B 2018/00357* (2013.01); *A61B 2018/00369* (2013.01); *A61B 2018/126* (2013.01); *A61B 2018/144* (2013.01); *A61B 2018/1475* (2013.01)

(58) Field of Classification Search
CPC ........... A61B 2018/00083; A61B 2018/00178; A61B 2018/00351; A61B 2018/00357; A61B 2018/00369; A61B 2018/126; A61B 2018/144; A61B 2018/1475; A61B 18/16; A61B 2017/00247; A61B 2018/00702; A61B 2018/00726; A61B 2018/00767; A61B 2018/1253
See application file for complete search history.

(56) References Cited

U.S. PATENT DOCUMENTS 4,527,560 A * 7/1985 Masreliez ............ A61B 18/082 219/233
5,021,045 A 6/1991 Buckberg et al.
5,047,026 A * 9/1991 Rydell ............... A61B 18/1482 606/48
5,190,528 A 3/1993 Fonger et al.
5,221,281 A * 6/1993 Klicek ............... A61B 18/1487 606/45
5,304,171 A * 4/1994 Gregory ............... A61N 5/0601 606/15
5,417,687 A * 5/1995 Nardella ............ A61B 17/3476 604/164.08
5,431,649 A 7/1995 Mulier et al.
5,676,662 A * 10/1997 Fleischhacker .... A61B 18/1492 600/374
5,676,670 A * 10/1997 Kim ............... A61B 17/320016 606/108
5,797,920 A * 8/1998 Kim ....................... A61B 17/11 606/108
5,871,469 A * 2/1999 Eggers ............... A61B 18/1206 604/114
5,910,129 A * 6/1999 Koblish ........... A61M 25/0043 604/95.03
5,941,876 A * 8/1999 Nardella ............ A61B 18/1482 606/45
6,004,319 A * 12/1999 Goble ................ A61B 18/1206 606/48
6,012,457 A 1/2000 Lesh
6,024,740 A * 2/2000 Lesh ...................... A61B 18/00 606/34
6,056,746 A * 5/2000 Goble ................ A61B 18/1482 606/48
6,074,386 A * 6/2000 Goble ................ A61B 18/1206 606/34
6,102,046 A * 8/2000 Weinstein .............. A61B 18/12 128/898
6,146,380 A 11/2000 Racz et al.
6,190,353 B1 2/2001 Makower et al.
6,193,717 B1 2/2001 Ouchi
6,231,546 B1 5/2001 Milo et al.
6,251,107 B1 * 6/2001 Schaer ............... A61B 18/1492 600/374
6,391,005 B1 * 5/2002 Lum ...................... A61B 5/053 600/506
6,475,226 B1 11/2002 Belef et al.
6,529,756 B1 * 3/2003 Phan .................. A61B 18/1492 600/374
6,544,230 B1 4/2003 Flaherty et al.
6,565,555 B1 * 5/2003 Ryan ...................... A61B 18/24 606/17
6,565,562 B1 * 5/2003 Shah .................. A61B 18/1492 128/898
6,602,248 B1 * 8/2003 Sharps ............... A61B 18/1402 606/32
6,645,199 B1 * 11/2003 Jenkins .............. A61B 18/1492 606/41
6,650,923 B1 11/2003 Lesh et al.
6,936,024 B1 * 8/2005 Houser .............. A61B 18/1492 604/22
7,048,733 B2 5/2006 Hartley et al.
7,070,596 B1 * 7/2006 Woloszko .......... A61B 18/1482 606/41
7,112,197 B2 9/2006 Hartley et al.
7,150,747 B1 * 12/2006 McDonald ........... A61B 18/148 606/45
7,194,294 B2 * 3/2007 Panescu ................. A61B 5/287 600/374
7,229,437 B2 * 6/2007 Johnson ................. A61B 5/287 606/41
7,270,662 B2 9/2007 Visram et al.
7,947,040 B2 * 5/2011 Davies ............... A61B 18/1492 606/45
8,092,450 B2 1/2012 Davies et al.
8,192,425 B2 6/2012 Mirza et al.
8,235,985 B2 8/2012 Saadat et al.
8,457,714 B2 6/2013 Shachar et al.
8,500,768 B2 8/2013 Cohen
8,679,107 B2 * 3/2014 Mirza ................ A61B 18/1482 606/33
8,834,384 B2 9/2014 Krishnan
8,882,697 B2 * 11/2014 Celermajer ........... A61F 2/2442 604/8
8,992,556 B2 3/2015 Chanduszko et al.
9,095,350 B2 8/2015 Condie et al.
9,179,932 B2 11/2015 Davies et al.
9,415,188 B2 8/2016 He
9,504,398 B2 11/2016 Krishnan
9,510,900 B2 * 12/2016 Abou-Marie ...... A61B 18/1492
9,585,692 B2 3/2017 Kurth et al.
9,597,146 B2 3/2017 Davies et al.
10,166,070 B2 1/2019 Davies et al.
10,172,632 B2 1/2019 Morero et al.
10,183,151 B2 1/2019 Alvarez et al.
10,485,569 B2 11/2019 Lenker et al.
10,493,259 B2 12/2019 Urbanski et al.
10,610,297 B2 4/2020 Leung et al.
10,631,915 B1 * 4/2020 Cosman ............. A61B 18/1492
10,639,060 B2 5/2020 Vardi et al.
10,716,920 B2 7/2020 Kurth et al.
10,820,925 B2 11/2020 Urbanski et al.
10,856,902 B2 12/2020 Leeflang et al.
11,007,016 B2 5/2021 Kusumoto
11,172,984 B2 11/2021 Sharma et al.
2001/0056280 A1 * 12/2001 Underwood ......... A61B 18/148 606/41
2002/0058905 A1 5/2002 Madrid et al.
2002/0095152 A1 * 7/2002 Ciarrocca ............ A61B 18/149 606/48
2002/0120259 A1 * 8/2002 Lettice ............... A61B 18/1492 606/32
2002/0177765 A1 * 11/2002 Bowe ................. A61B 18/1492 600/374
2002/0193781 A1 * 12/2002 Loeb .................. A61B 18/1402 606/15
2003/0009164 A1 * 1/2003 Woloszko .......... A61B 18/1492 606/41
2003/0083613 A1 5/2003 Schaer
2003/0088245 A1 * 5/2003 Woloszko ............ A61B 18/148 606/41
2003/0109809 A1 6/2003 Jen et al.
2003/0114833 A1 * 6/2003 Thompson ........ A61M 25/0147 604/528
2003/0163153 A1 8/2003 Scheib
2004/0082860 A1 * 4/2004 Haissaguerre ......... A61B 5/287 600/466
2004/0133113 A1 7/2004 Krishnan
2004/0143261 A1 7/2004 Hartley et al.
2004/0143262 A1 * 7/2004 Visram ............. A61B 18/1492 606/45

(56) References Cited

U.S. PATENT DOCUMENTS

2004/0167509 A1* 8/2004 Taimisto ............ A61B 18/1492 606/41
2004/0186469 A1* 9/2004 Woloszko ............ A61B 5/015 606/41
2004/0220461 A1 11/2004 Schwartz
2004/0220462 A1* 11/2004 Schwartz ............ A61B 5/287 600/374
2005/0033288 A1 2/2005 Auth et al.
2005/0065498 A1 3/2005 McFerran
2005/0149097 A1 7/2005 Regnell et al.
2005/0154386 A1* 7/2005 West ............ A61B 18/1492 606/41
2005/0171478 A1 8/2005 Selmon et al.
2005/0215994 A1 9/2005 Solomon
2006/0074484 A1 4/2006 Huber
2006/0079873 A1 4/2006 Scopton et al.
2006/0178666 A1 8/2006 Cosman et al.
2006/0241583 A1 10/2006 Malecki et al.
2006/0287650 A1* 12/2006 Cao ............ A61B 18/1492 606/41
2007/0016182 A1* 1/2007 Lipson ............ A61B 18/12 606/34
2007/0073389 A1 3/2007 Bolduc et al.
2008/0119846 A1* 5/2008 Rioux ............ A61B 18/1482 606/41
2008/0140073 A1 6/2008 Schwartz
2008/0154259 A1 6/2008 Gough et al.
2008/0208184 A1* 8/2008 Davies ............ A61B 18/1492 606/34
2008/0215085 A1* 9/2008 Whisenant ......... A61B 18/1492 606/213
2009/0005774 A1 1/2009 Fernald
2009/0012517 A1 1/2009 de la Rama et al.
2009/0093803 A1* 4/2009 Herrin ............ A61B 18/1492 606/33
2009/0099555 A1* 4/2009 Viohl ............ A61N 1/37 606/1
2010/0191142 A1 7/2010 Paul et al.
2011/0112564 A1 5/2011 Wolf
2011/0166519 A1* 7/2011 Nguyen ............ A61N 1/403 604/114
2011/0224666 A1* 9/2011 Davies ............ A61B 18/1492 606/33
2012/0232546 A1 9/2012 Mirza et al.
2012/0323231 A1 12/2012 Atwell
2013/0046305 A1* 2/2013 Davies ............ A61B 18/1492 606/45
2013/0317528 A1 11/2013 Anderson et al.
2014/0039492 A1* 2/2014 Long ............ A61B 18/1477 606/41
2014/0066917 A1* 3/2014 Cosman, Jr. ........... A61B 18/18 606/33
2014/0100561 A1* 4/2014 Biadillah ............ A61B 18/18 606/33
2014/0107644 A1 4/2014 Falwell et al.
2014/0121658 A1* 5/2014 Cosman, Jr. ....... A61B 18/1477 606/33
2014/0142607 A1 5/2014 Cage et al.
2014/0206987 A1* 7/2014 Urbanski ............ A61M 5/007 600/424
2014/0228841 A1* 8/2014 Davies ............ A61B 18/1492 606/45
2014/0364844 A1* 12/2014 Van Wyk ........... A61B 18/1477 606/37
2015/0157353 A1 6/2015 Lenker et al.
2015/0173827 A1* 6/2015 Bloom ............ A61B 18/148 606/39
2015/0182255 A1 7/2015 Shivkumar
2015/0223866 A1* 8/2015 Buelna ............ A61K 31/045 600/3
2015/0265337 A1* 9/2015 Bloom ............ A61B 18/1485 606/48
2015/0265344 A1 9/2015 Aktas et al.
2015/0297246 A1* 10/2015 Patel ............ A61B 17/3478 606/79
2016/0045219 A1 2/2016 Guala et al.
2016/0235469 A1* 8/2016 Prisco ............ A61B 18/1485
2016/0262795 A1 9/2016 Urbanski et al.
2016/0374751 A1* 12/2016 Davies ............ A61B 18/1477 606/48
2017/0071667 A1* 3/2017 Leung ............ A61B 90/39
2017/0105762 A1* 4/2017 Bloom ............ A61B 17/3468
2017/0135559 A1 5/2017 Horrisberger et al.
2017/0348049 A1* 12/2017 Vrba ............ A61B 18/1492
2017/0360498 A1 12/2017 Davies et al.
2018/0028258 A1 2/2018 Zamarripa et al.
2018/0064415 A1 3/2018 Zhai et al.
2018/0064915 A1 3/2018 Kurth et al.
2018/0070982 A1 3/2018 Kimmel et al.
2018/0146839 A1* 5/2018 Friedlander .......... A61B 1/0005
2018/0263658 A1 9/2018 Drasler
2018/0289388 A1 10/2018 Lenker et al.
2018/0333162 A1 11/2018 Saab
2019/0134349 A1 5/2019 Cohn et al.
2019/0274581 A1 9/2019 Mosesov
2019/0374254 A1* 12/2019 Arevalos .......... A61B 17/32053
2019/0374281 A1* 12/2019 Davies ............ A61B 18/1492
2020/0008869 A1* 1/2020 Byrd ............ A61B 18/1206
2020/0038091 A1* 2/2020 Cao ............ A61B 18/14
2020/0060710 A1 2/2020 Urbanski et al.
2020/0196908 A1 6/2020 Ben-Haim et al.
2020/0352647 A1* 11/2020 Davies ............ A61B 17/3478
2021/0038892 A1 2/2021 Velasco Valcke
2021/0068892 A1* 3/2021 Urbanski ............ A61B 5/4836
2021/0077419 A1* 3/2021 Buelna ............ A61B 18/1492
2021/0121227 A1 4/2021 Davies et al.
2021/0353354 A1 11/2021 Schuler et al.
2021/0353355 A1 11/2021 Schuler et al.
2021/0401483 A1 12/2021 Highsmith et al.
2022/0061884 A1 3/2022 Howard et al.
2022/0061909 A1 3/2022 Howard et al.
2022/0061911 A1 3/2022 Howard et al.
2022/0110577 A1 4/2022 Highsmith et al.

FOREIGN PATENT DOCUMENTS

EP 1728462 A2 12/2006
EP 2037812 3/2009
WO WO 2002/058780 8/2002
WO WO 2005/046487 5/2005
WO WO 2013/101632 7/2013
WO WO 2014/089373 6/2014
WO 2016205328 A1 12/2016
WO WO 2018/165277 9/2018
WO WO-2018163899 A1 * 9/2018 ............ A61B 18/14
WO 2018187244 A2 10/2018
WO 2020018304 A1 1/2020
WO WO 2021/014316 1/2021
WO WO 2021/231465 11/2021
WO WO 2022/046777 3/2022

OTHER PUBLICATIONS

U.S. Appl. No. 16/896,604, filed Jun. 9, 2020, Tubular Large Bore Transseptal Crossing Sheath.

U.S. Appl. No. 16/896,648, filed Jun. 9, 2020, Method For Single Pass Large Bore Transseptal Crossing.

Clinical Analysis of RF Transseptal Puncture, NRG Transseptal Needle, USA, Canada, Baylis Medical Company, Inc., 2016.

International Search Report and Written Opinion, Application No. PCT/US2021/031827, dated Oct. 20, 2021.

International Search Report and Written Opinion in corresponding International Patent Application No. PCT/US2021/047361, mailed Jan. 27, 2022, in 10 pages.

Extended European Search Report of the European Patent Office in the related European Patent Appl. No. 21804279.4, dated Apr. 26, 2024, 9 pages.

(56) References Cited

OTHER PUBLICATIONS

Final Office Action of the United States Patent and Trademark Office in related U.S. Appl. No. 18/752,720, dated Jul. 29, 2025, 13 pages.

* cited by examiner 2B
206
115
210
104
106
A
A
200
111
102
114
118
116
210

210
202
206

210
212
208
206
214

104

206
115
210
104
208
111
114
228
226
220
224
222
116
118
210

TUBULAR LARGE BORE TRANSSEPTAL CROSSING SHEATH

CROSS-REFERENCE TO RELATED APPLICATIONS

This application claims the priority benefit under 35 U.S.C. § 119(e) of U.S. Provisional Application No. 63/024,986, filed May 14, 2020, the entirety of which is hereby incorporated by reference herein.

BACKGROUND OF THE INVENTION

Transseptal crossing is used to access the left atrium crossing from the right atrium through the septal wall for any of a variety of electrophysiology (EP) or structural heart procedures. For example, the left atrium is routinely accessed to assess hemodynamics and/or perform mitral valvuloplasty, or to accommodate transvascular atrial fibrillation (AF) ablation procedures.

Crossing the septum normally requires locating and puncturing the fossa ovalis to access the left atrium. Locating the fossa ovalis may be accomplished using fluoroscopy and ultrasound, and potentially echocardiography.

Mechanical puncture through the tissue of the fossa ovalis can be accomplished using a piercing tool such as a standard Brockenbrough needle as is understood in the art. Alternatively, a transseptal needle having a radio frequency energized tip may be used, such as those produced by Baylis Medical Company, Inc.

The foregoing devices and techniques have proven useful in a variety of EP and structural heart procedures, in which the procedural access sheath is often no larger than about 3.667 mm (11 French). However, a growing number of procedures such as left atrial appendage occlusion device implantation and various Mitral valve replacement or repair require "large bore" access, which is not possible using the above techniques alone.

Instead, traditional transseptal puncture is normally carried out with small bore sheaths ranging from 8 Fr to 11 Fr which are then exchanged over stiff guidewires for the large bore sheaths with outer dimensions as large as 24 Fr in the case of the MitraClip Steerable Guide Catheter. Dilators for the transseptal sheaths usually accommodate 0.032 in. wires, however Baylis has introduced a small bore transseptal sheath with a dilator that accommodates a 0.035 in. wire. Regardless of the transseptal sheath, the operator must utilize a number of additional pieces of equipment including the small bore transseptal sheath and dilator, and often a 0.025 in. "stiff" pigtail wire (Baylis, Toray) to use as a rail to drive the small bore transseptal sheath and dilator before switching to a 0.035 in. guidewire (Amplatz extra stiff or Safari) to drive the large bore sheath safely into the LA. The entire small bore sheath must be driven into the LA to make the switch to the appropriate stiff 0.035 in. guidewire to drive the large bore sheath.

Thus, there remains a need for a transseptal crossing system that is based upon a 0.035 inch guidewire access, that enables single pass crossing of larger sheaths, such as the Boston Scientific Watchman guide sheath, Medtronic Flexcath and others known in the art or yet to be released.

SUMMARY OF THE INVENTION

In general, the present invention provides a single pass transseptal crossing device, for enabling large bore access in a single pass. The system includes an insulated cannula with a conductive tip positionable through the dilator of a large bore sheath. The tip of the cannula is expressed distal to the tip of the dilator. The insulated cannula can serve as an electrical conduit of RF energy. The cannula can be energized to deliver RF energy directly to tissues and/or through a separate conductive wire or obturator. An insulated wire or obturator can thus be independently energized or can be energized passively via the energized cannula. The cannula may be 0.050" outer diameter (OD) and approximately 0.038" inner diameter (ID) allowing delivery of a 0.035" wire which together (stiff 0.035 wire and 0.050 cannula) creates a sturdy rail to drive large bore dilators and sheaths in a single pass. The tip of the cannula can be scalloped to deliver high density current to the scalloped edges for improved cutting. The system permits irrigation with hypotonic saline or D5W to preferentially drive current through the myocardium.

Thus, there is provided in accordance with one aspect of the present invention a single pass, large bore transseptal crossing catheter, such as for accessing the left atrium of the heart. The catheter comprises an elongate, flexible tubular body, having a proximal end, a distal end and an electrically conductive sidewall defining a central lumen. An insulation layer surrounds the sidewall and leaving exposed a first distal electrode tip. An inner conductive wire having a second distal electrode tip, is axially movably extendable through the central lumen. A tubular insulation layer is provided in between the wire and the electrically conductive sidewall.

The first distal electrode tip may comprise an annular conductive surface at the distal end of the tubular body. The second distal electrode tip may be concentrically extendable through the annular conductive surface. The first distal electrode tip may comprise at least one distal projection, or at least two or three projections and in one implementation comprises a scalloped distal edge.

The second distal electrode may comprise a smooth, hemispherical surface, or may be provided with a sharpened distally facing projection. The catheter may additionally comprise an annular lumen extending between the tubular body and the wire, from the proximal hub to an exit port at the distal end.

In accordance with a further aspect of the present invention, there is provided an introducer sheath, for enabling a single pass, large bore transseptal crossing. The introducer sheath comprises an elongate, flexible tubular body, having a proximal end, a distal end and an electrically conductive sidewall defining a central lumen. A tubular insulation layer may surround the sidewall, leaving exposed an annular conductive surface at the distal end. A proximal hub may be provided on the tubular body, having at least one access port in communication with the central lumen. A connector may be carried by the proximal end, in electrical communication with the conductive sidewall. The distal conductive surface may comprise at least one distal projection, or at least two or three projections and in one implementation comprises a scalloped distal edge.

There is also provided a method of accessing the left atrium with a large bore catheter in a single pass. The method comprises providing a single pass, large bore transseptal crossing catheter; positioning the distal end in contact with a fossa ovalis; and energizing the distal end to enable passage of the distal end into the left atrium.

The energizing step may comprise energizing a first distal electrode tip on a conductive tubular cannula and/or energizing a second distal electrode tip on an RF core wire. The first and second distal electrode tips may be energized in a bipolar mode.

The method may comprise accessing the left atrium, energizing the second distal electrode tip, advancing the wire through the fossa ovalis, thereafter energizing the first distal electrode tip and advancing the cannula into the left atrium.

A large bore access sheath may thereafter be advanced over the transseptal crossing catheter and into the left atrium, and the transseptal crossing catheter may then be removed, leaving the large bore access sheath extending into the left atrium.

An index procedure catheter may be advanced through the large bore access sheath and into the left atrium. The index procedure catheter may be configured to deliver a left atrial appendage implant such as an occlusion device, or to accomplish a mitral valve repair or replacement.

DETAILED DESCRIPTION OF THE PREFERRED EMBODIMENT

Figure 1:
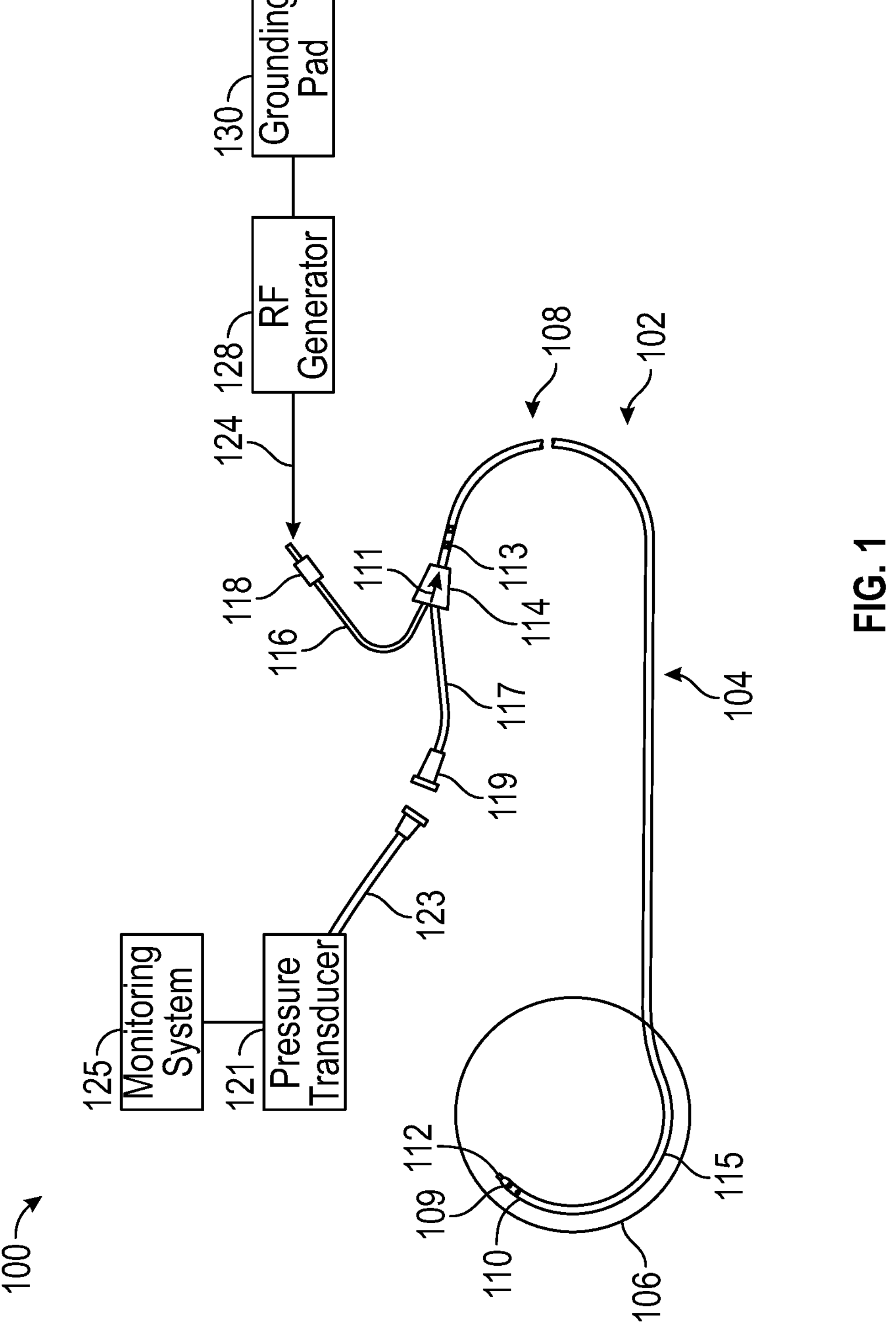
FIG. 1 schematically illustrates a transseptal crossing system in accordance with the present invention.

FIG. 1 illustrates an embodiment of a tissue penetrating apparatus 102 in a transseptal crossing system 100. Apparatus 102 comprises an elongate tubular body 104 having a distal region 106, and a proximal region 108. Distal region 106 is adapted to be inserted within and along a lumen of a body of a patient, such as a patient's vasculature, and maneuverable therethrough to a desired location proximate material, such as tissue, to be perforated.

Figures 2, 2A, 2B:
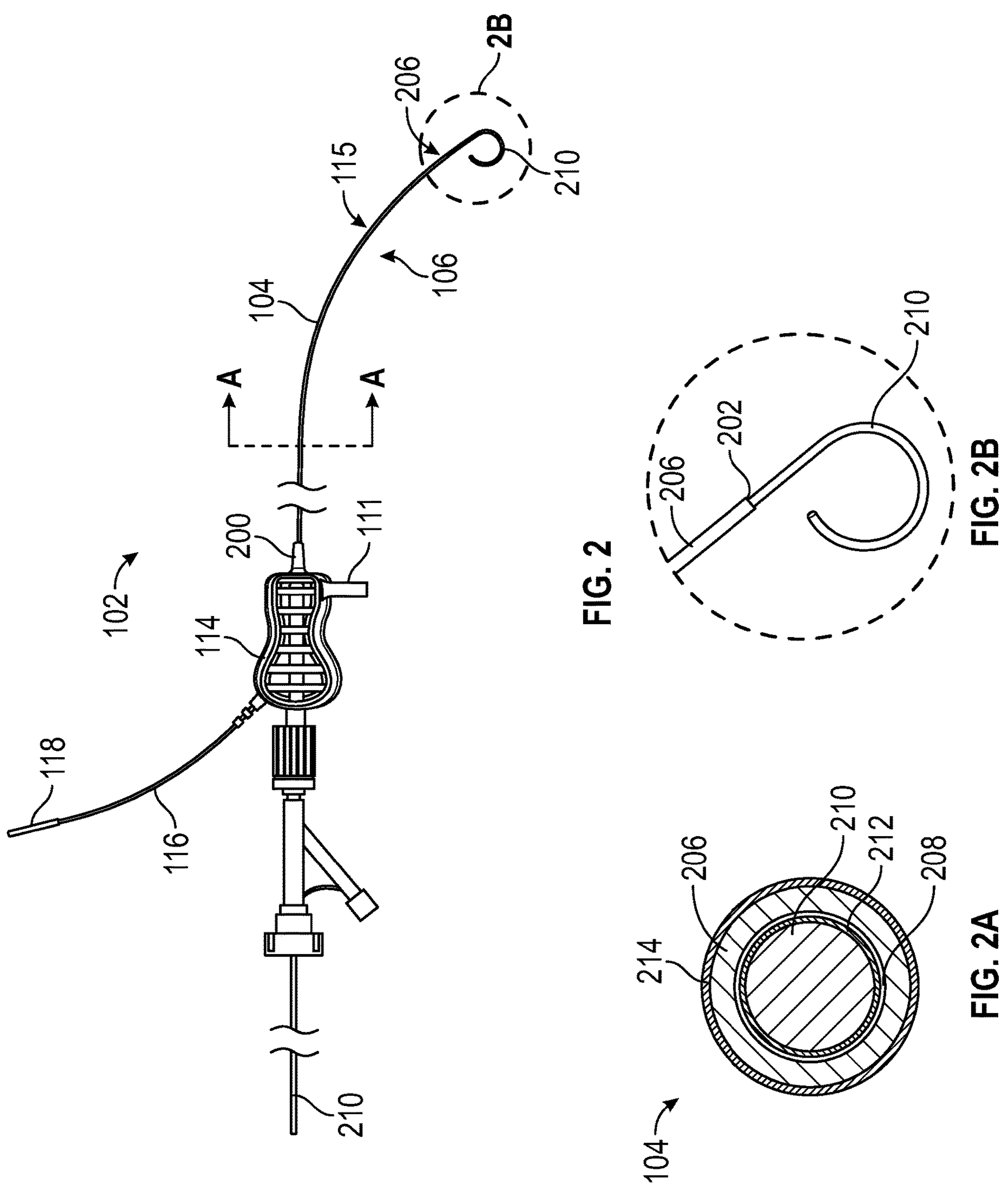
FIG. 2 is a side elevational view of an RF needle in accordance with the present invention.
FIG. 2A is a cross section taken along the line A-A in FIG. 2.
FIG. 2B is a detail view of the distal tip of the needle in FIG. 2.

In some embodiments, the tubular body 104 may have at least one lumen extending from proximal region 108 to distal region 106 such as lumen 208 shown in FIG. 2A. Tubular body 104 may be constructed of a biocompatible polymer material jacket typically with a metal core that provides column strength to apparatus 102. The tubular body 104 is sufficiently stiff to permit a dilator 84 and a large bore guiding sheath 12 (See FIG. 6) to be easily advanced over apparatus 102 and through a perforation. Examples of suitable materials for the tubular portion of tubular body 104 are stainless steel, nitinol, polyetheretherketone (PEEK), nylon, and polyimide. In the illustrated embodiment, the outer diameter along the tubular portion of tubular body 104 may taper down to distal region 106. In alternate embodiments, the outer diameter along tubular body 104 remains substantially constant from proximal region 108 to distal region 106.

Distal region 106 comprises a softer polymer material with an optional embedded braid or coil so that it is pliable and atraumatic when advanced through vasculature. In some embodiments, the material is also formable (e.g., Nitinol or stainless steel with a polymer jacket), so that its shape can be changed during manufacturing, typically by exposing it to heat while it is fixed in a desired shape. In an alternate embodiment, the shape of distal region is modifiable by the operator during use. An example of a suitable plastic is PEBAX (a registered trademark of Atofina Chemicals, Inc.). In the present embodiment, the distal region 106 comprises a curve portion 115.

As the distal region 106 is advanced out of a guiding sheath, it may have a preset curve so that it curls away from the general axis of the sheath which helps ensure that energy delivery tip 112 is not in a position to inadvertently injure unwanted areas within a patient's heart after trans-septal perforation. Curve length may be about 4 cm (about 1.57") to about 6 cm (about 2.36") and the curve may traverse about 225 to about 315 degrees of the circumference of a circle. For example, the curve may be about 5 cm in length and may traverse about 270 degrees of the circumference of a circle. Such an embodiment may be useful to avoid unwanted damage to cardiac structures.

In some embodiments, curve portion 115 begins about 0.5 cm to about 1.5 cm proximal to energy delivery device 112, leaving an approximately 1 cm (about 0.39") straight portion in the distal region 106 of apparatus 102. This ensures that this initial portion of apparatus 102 will exit dilator 84 (see FIG. 6) without curving, enabling the operator to easily position the apparatus 102, for example, against a septum as described further below. This feature further ensures that the distal region 106 of apparatus 102 will not begin curving within the atrial septum.

Distal region 106 may have a smaller outer diameter compared to the remainder of tubular body 104 so that dilation of a perforation is limited while the distal region 106 is advanced through the perforation. Limiting dilation seeks to ensure that the perforation will not cause hemodynamic instability once apparatus 102 is removed. In some embodiments, the outer diameter of distal region 106 may be no larger than about 0.8 mm to about 1.0 mm. For example, the outer diameter of distal region 106 may be about 0.9 mm (about 0.035"). This is comparable to the distal outer diameter of the trans-septal needle that is traditionally used for creating a perforation in the atrial septum. Similarly, in some embodiments, the outer diameter of tubular body 104 may be no larger than about 0.040" to about 0.060". For example, the outer diameter of tubular body 104 may be about 0.050" (1.282 mm), which is also comparable to the trans-septal needle dimensions.

Distal region 106 terminates at functional tip region 110, which comprises an energy delivery component and optionally also as an ECG measuring device. Functional tip region 110 comprises at least one energy delivery tip 112 made of a conductive and optionally radiopaque material, such as stainless steel, tungsten, platinum, or another metal. One or more radiopaque markings may be affixed to tubular body 104 to highlight the location of the transition from distal region 106 to the remainder of tubular body 104, or other important landmarks on apparatus 102. Alternately, the entire distal region 106 of apparatus 102 may be radiopaque. This can be achieved by filling the polymer material, for example PEBAX, used to construct distal region 106 with radiopaque filler. An example of suitable radiopaque filler is Bismuth. Distal region 106 may contain at least one opening 109 which is in fluid communication with main lumen 200 (FIG. 2A) as described further below.

In the illustrated embodiment, proximal region 108 comprises a hub 114, to which are attached a catheter connector cable 116, and connector 118. Tubing 117 and adapter 119 are attached to hub 114 as well. Proximal region 108 may also have one or more depth markings 113 to indicate distances from functional tip region 110, or other important landmarks on apparatus 102. Hub 114 comprises a curve direction or orientation indicator 111 that is located on the same side of apparatus 102 as the curve 115 in order to indicate the direction of curve 115. Orientation indicator 111 may comprise inks, etching, or other materials that enhance visualization or tactile sensation. One or more curve direction indicators may be used and they may be of any suitable shape and size and a location thereof may be varied about the proximal region 108.

In the illustrated embodiment, adapter 119 is configured to releasably couple apparatus 102 to an external pressure transducer 121 via external tubing 123. External pressure transducer 121 is coupled to a monitoring system 125 that converts a pressure signal from external pressure transducer 121 and displays pressure as a function of time. Catheter connector cable 116 may connect to an optional Electrocardiogram (ECG) interface unit via connector 118. An optional ECG connector cable connects an ECG interface unit to an ECG recorder, which displays and captures ECG signals as a function of time. A generator connector cable may connect the ECG interface unit to an energy source such as a generator (not illustrated). In this embodiment, the ECG interface unit can function as a splitter, permitting connection of the electrosurgical tissue piercing apparatus 102 to both an ECG recorder and generator simultaneously. ECG signals can be continuously monitored and recorded and the filtering circuit within the ECG interface unit and may permit energy, for example RF energy, to be delivered from generator 128 through electrosurgical apparatus 102 without compromising the ECG recorder.

In another embodiment (not shown) of apparatus 102, there may be a deflection control mechanism associated with the distal region 106 of apparatus 102 and an operating mechanism to operate said control mechanism associated with the proximal region 108 of apparatus 102. One or two or more pull wires may extend from a proximal control to the distal region 106 to actively deflect the distal region 106 as will be understood in the art. The control mechanism may be used to steer or otherwise actuate at least a portion of distal region 106.

Generator 128 may be a radiofrequency (RF) electrical generator that is designed to work in a high impedance range. Because of the small size of energy delivery tip 112, the impedance encountered during RF energy application is very high. General electrosurgical generators are typically not designed to deliver energy in these impedance ranges, so only certain RF generators can be used with this device. In one embodiment, the energy is delivered as a continuous wave at a frequency between about 400 kHz and about 550 kHz, such as about 460 kHz, a voltage of between 100 to 200 V RMS and a duration of up to 99 seconds. A grounding pad 130 is coupled to generator 128 for attaching to a patient to provide a return path for the RF energy when generator 128 is operated in a monopolar mode.

Other embodiments could use pulsed or non-continuous RF energy. Some embodiments for pulsed radio frequency energy have radio frequency energy of not more than about 60 watts, a voltage from about 200 Vrms to about 400 Vrms and a duty cycle of about 5% to about 50% at about from slightly more than 0 Hz to about 10 Hz. More specific embodiments include radio frequency energy of not more than about 60 watts, a voltage from about 240 Vrms to about 300 Vrms and a duty cycle of 5% to 40% at 1 Hz, with possibly, the pulsed radio frequency energy being delivered for a maximum of 10 seconds. In one example, the generator can be set to provide pulsed radio frequency energy of not more than about 50 watts, a voltage of about 270 Vrms, and a duty cycle of about 10% at 1 Hz. Alternatively, the pulsed radio frequency energy could comprise radio frequency energy of not more than about 50 watts, a voltage of about 270 Vrms, and a duty cycle of about 30% at 1 Hz.

In still other embodiments of apparatus 102, different energy sources may be used, such as radiant (e.g. laser), ultrasound, thermal or other frequencies of electrical energy (e.g. microwave), with appropriate energy sources, coupling devices and delivery devices depending upon the desired clinical performance.

Additional details of the tissue penetration apparatus 102 are described in connection with FIG. 2. Referring to FIGS. 2 and 2A, the tubular body 104 comprises a cannula 206 such as a 0.050" cannula having a central lumen 208 extending therethrough. The lumen 208 is dimensioned to slidably receive a guide wire 210 such as an 0.035" guidewire. In certain implementations of the invention, it may be desirable to electrically isolate the guide wire 210 from the cannula 206. This may be accomplished by providing a tubular insulation layer 212 positioned between the guide wire 210 and the cannula 206. In the illustrated embodiment, the insulation layer 212 comprises a coating or tubular sleeve surrounding the guide wire 210. A further tubular insulation layer 214 may be provided on the outside of the cannula 206 to electrically isolate the cannula 206 from the patient.

Referring to FIG. 2B, there is illustrated a detail view of the distal end 202 of cannula 206, having a guide wire 210 extending therethrough. The guide wire 210 may comprise a pigtail or other curved distal end as is understood in the art.

Figure 3:
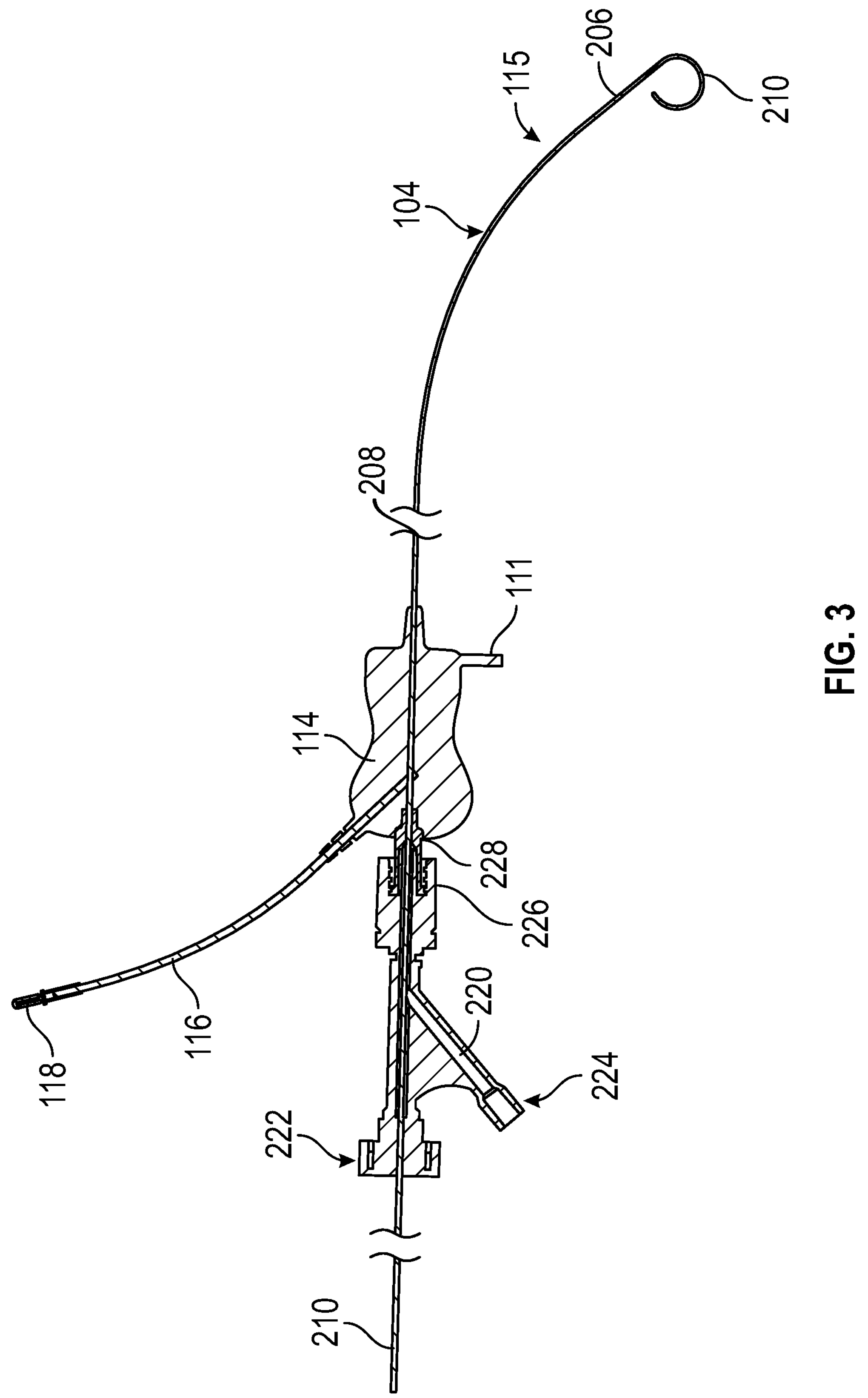
FIG. 3 is a cross sectional view through the needle of FIG. 2.

Referring to FIG. 3, the tissue penetrating apparatus 102 may additionally be provided with a Y connector 220, having a proximal guide wire access port 222 and a flush port 224 in communication with the distal region 106 such as via exit port 109 (FIG. 1) or cannula 206 central lumen 208. The Y connector 220 may be provided with a distal first connector 226 configured to cooperate with a second complementary connector 228 on the proximal end of the hub 114. First connector 226 and second connector 228 may be complementary components of a standard luer connector as is understood in the art. Alternatively, the hub 114 and Y connector 220 may be formed as an integral unit.

Figure 4A:
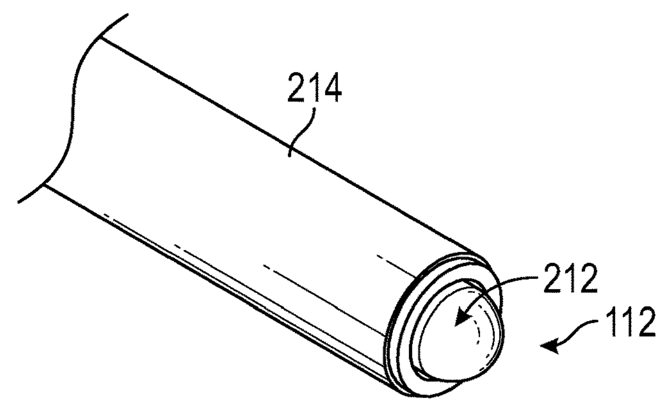
FIG. 4A-4C are detail views of the distal energy delivery tip of one implementation of the invention.
Figure 4B:
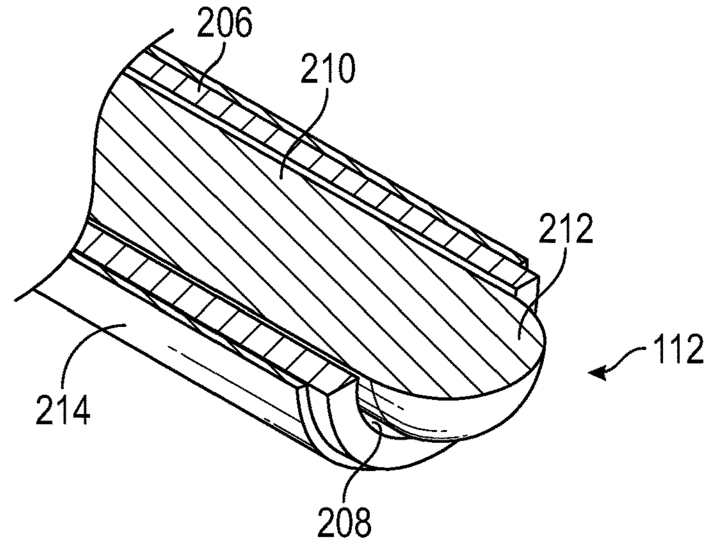
Figure 4C:
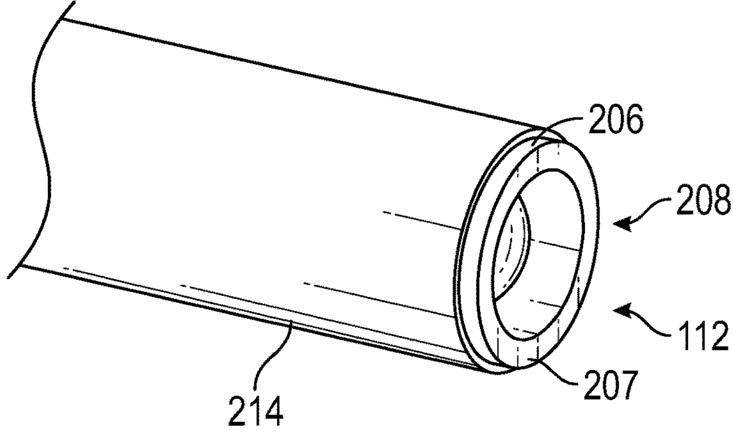

FIGS. 4A-4C illustrate the axial slidability of the guidewire 210 within the cannula 206. In FIG. 4C, the guidewire has been proximally retracted into the central lumen 208 so that the leading surface of the system is an annular charge transfer surface 207, which comprises a distal end face of the cannula 206. The insulation layer 214 on cannula 206 may extend distally all the way to the edge of the end face of the cannula 206, or to no more than 2 mm or 1 mm or less proximally of the end face of the cannula 206. The system thus permits delivering RF energy from either the guidewire alone, or the cannula alone or both, depending upon the desired clinical performance.

The separately insulated cannula 206 and guidewire can be configured to deliver bipolar electricity to the distal tip. The cannula 206 can be used as the ground path and replace the body pad or other electrode, which may provide desirable impedance characteristics depending upon the desired clinical performance.

Figure 5A:
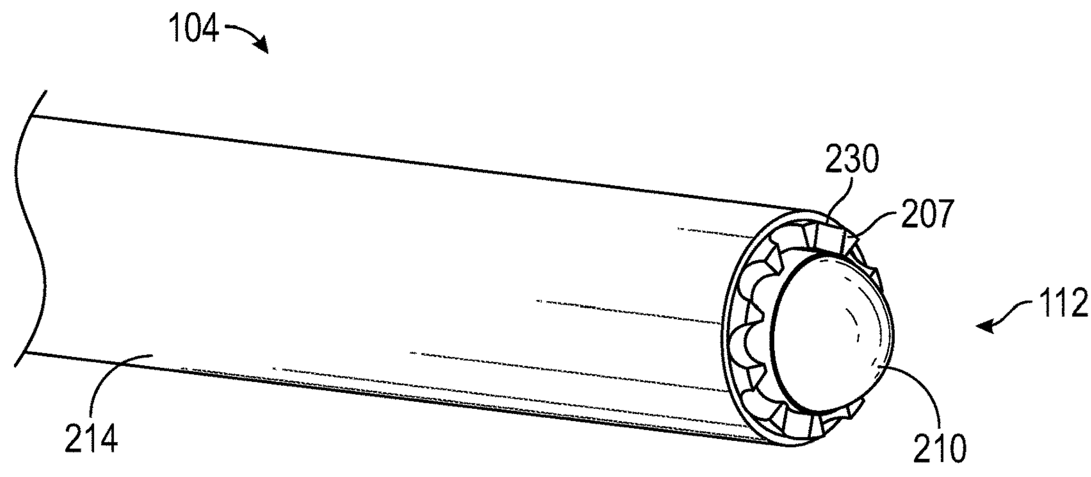
FIG. 5A-5C are detail views of the distal energy delivery tip of another implementation of the invention.
Figure 5B:
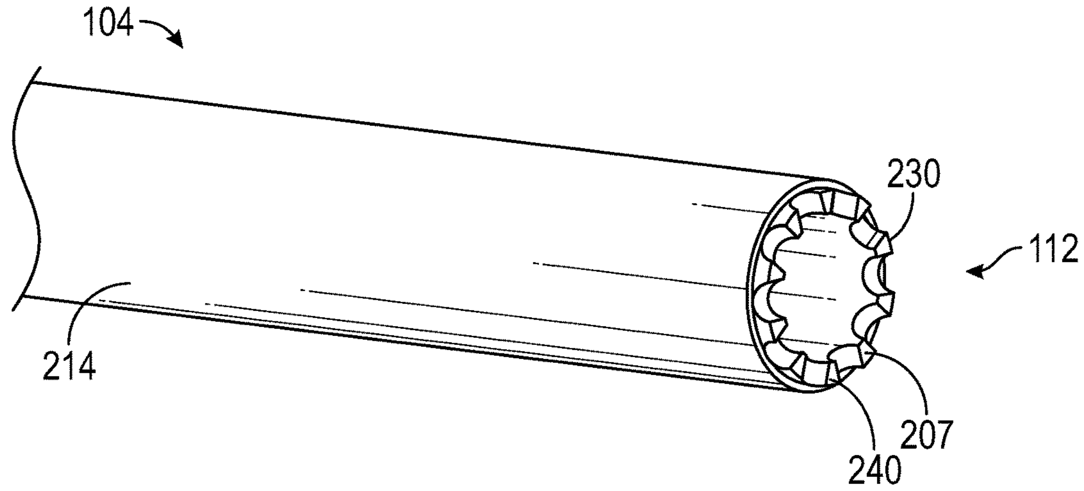
Figure 5C:
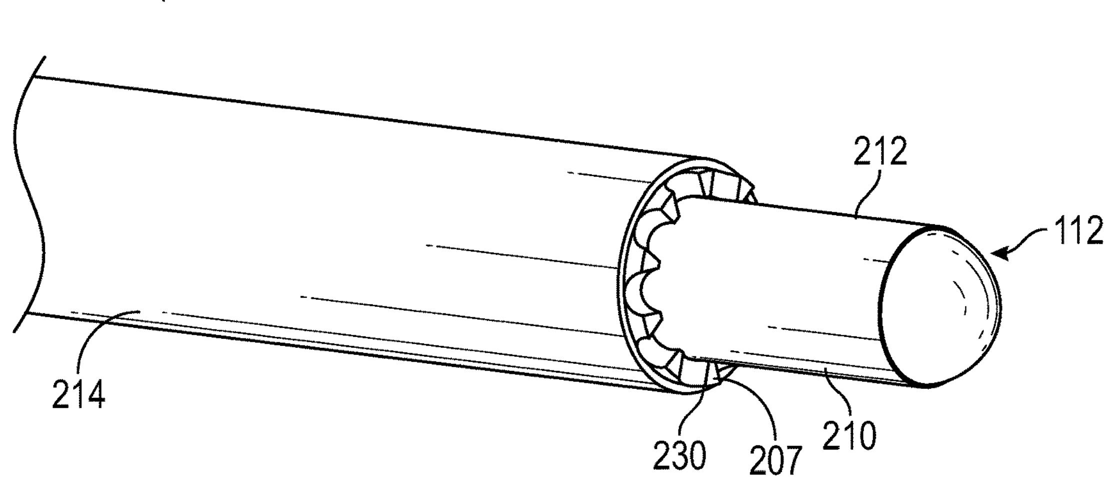

FIGS. 5A-5C illustrate a modified distal end face of the cannula 206. At least one distal extension 240 is carried by the cannula 206, to provide a site of enhanced energy density on the leading charge transfer surface 207 carried by the projection 240. At least two or four or more projections 240 may be provided, such as 10 as illustrated in FIG. 5B, creating scalloped surface with a plurality of circumferentially spaced apart distal transfer surfaces 207.

One method of delivering a large bore catheter in a single pass using the transseptal puncture system of the present invention may be as follows.

1. Advance a guidewire (GW) into the superior vena cava (SVC) and deliver a large bore catheter (e.g., left atrial appendage occlusion device; mitral valve repair or replacement; intra atrial adjustable annuloplasty device) with a dilator to the SVC.
2. Withdraw GW inside of the dilator.
3. Withdraw the large bore sheath and the dilator down to the right atrium.
4. Steer the sheath and dilator into position in the interatrial septum, specifically tenting the septum with the dilator.
5. Deliver the cannula and GW into position with the cannula extending distally beyond the dilator and the GW distally beyond the cannula and in contact with the fossa ovalis. 5*a*. If necessary for positioning purposes, withdraw cannula proximal to the bend of the steerable sheath, then step 6.
6. Activate the distal tip of the GW with RF energy, and pass the GW through the septum and into the left atrium (LA).
7. Drive the cannula, dilator and sheath distally through the septum and into the LA.
8. If the cannula cannot pass through the septum into the LA, activate the distal tip of the cannula with RF energy and advance the cannula into the LA.
9. Drive the dilator and the large bore sheath over the access cannula and into the LA.
10. Withdraw the cannula and dilator, and introduce the index procedure catheter through the large bore sheath.

As will be appreciated by those of skill in the art, the GW and cannula can alternatively be simultaneously operated in monopolar mode; either the GW or cannula can be energized separately; or the GW and cannula can be operated in bipolar mode, depending upon the desired clinical performance.

Figure 6:
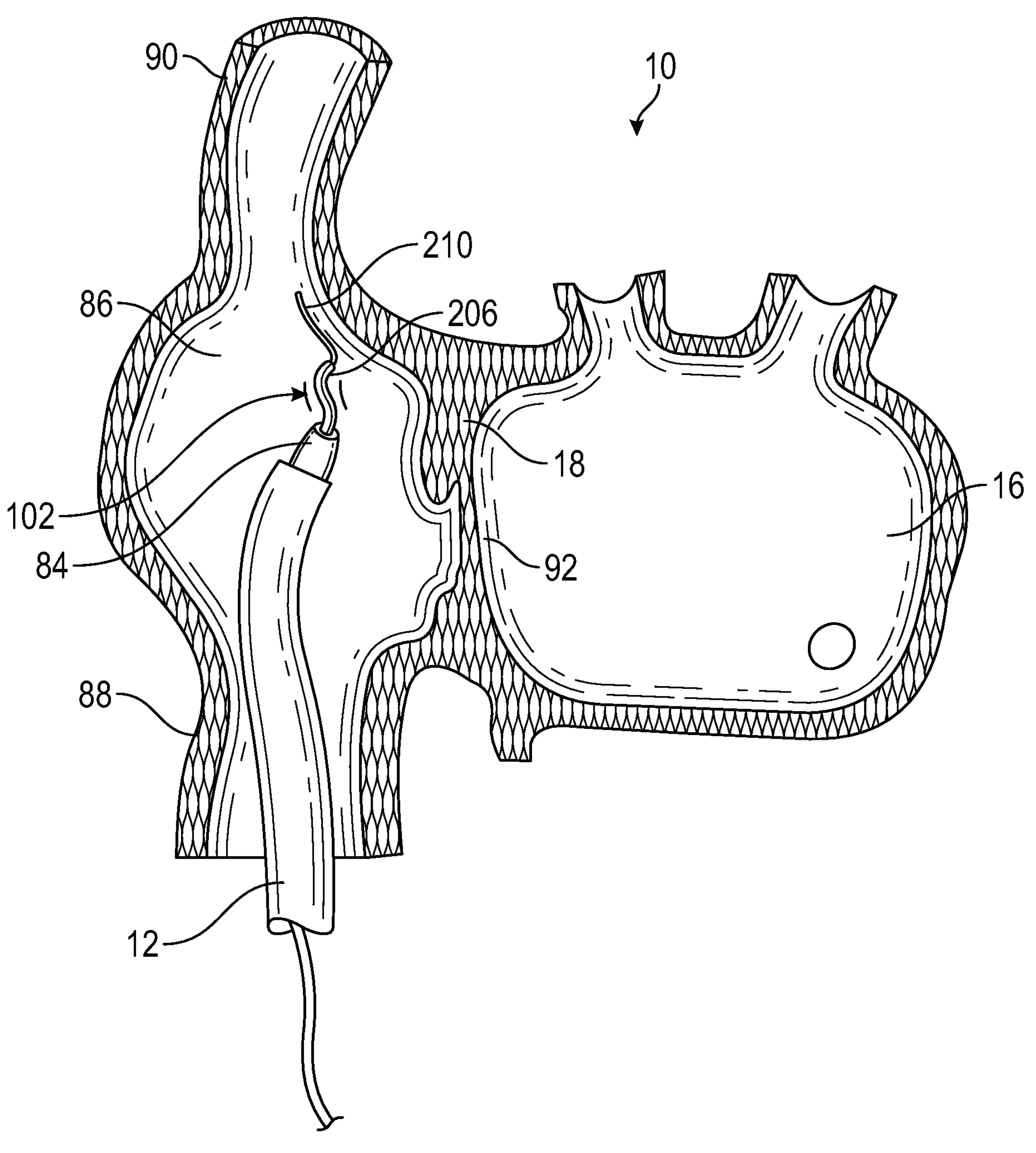
FIG. 6 is a schematic cross section of a portion of a human heart, having a transseptal crossing system of the present invention positioned in the right atrium.

Thus, referring to FIG. 6, there is illustrated a schematic cross-section of a portion of the heart 10. The right atrium 86 is in communication with the inferior vena cava 88 and the superior vena cava 90. The right atrium 86 is separated from the left atrium 16 by the intraatrial septum 18. The fossa ovalis 92 is located on the intraatrial septum 18. As seen in FIG. 6, a large bore transseptal sheath 12 may have a dilator 84, both riding over the cannula 206 and guidewire 210, all positioned within the right atrium 86.

Figure 7:
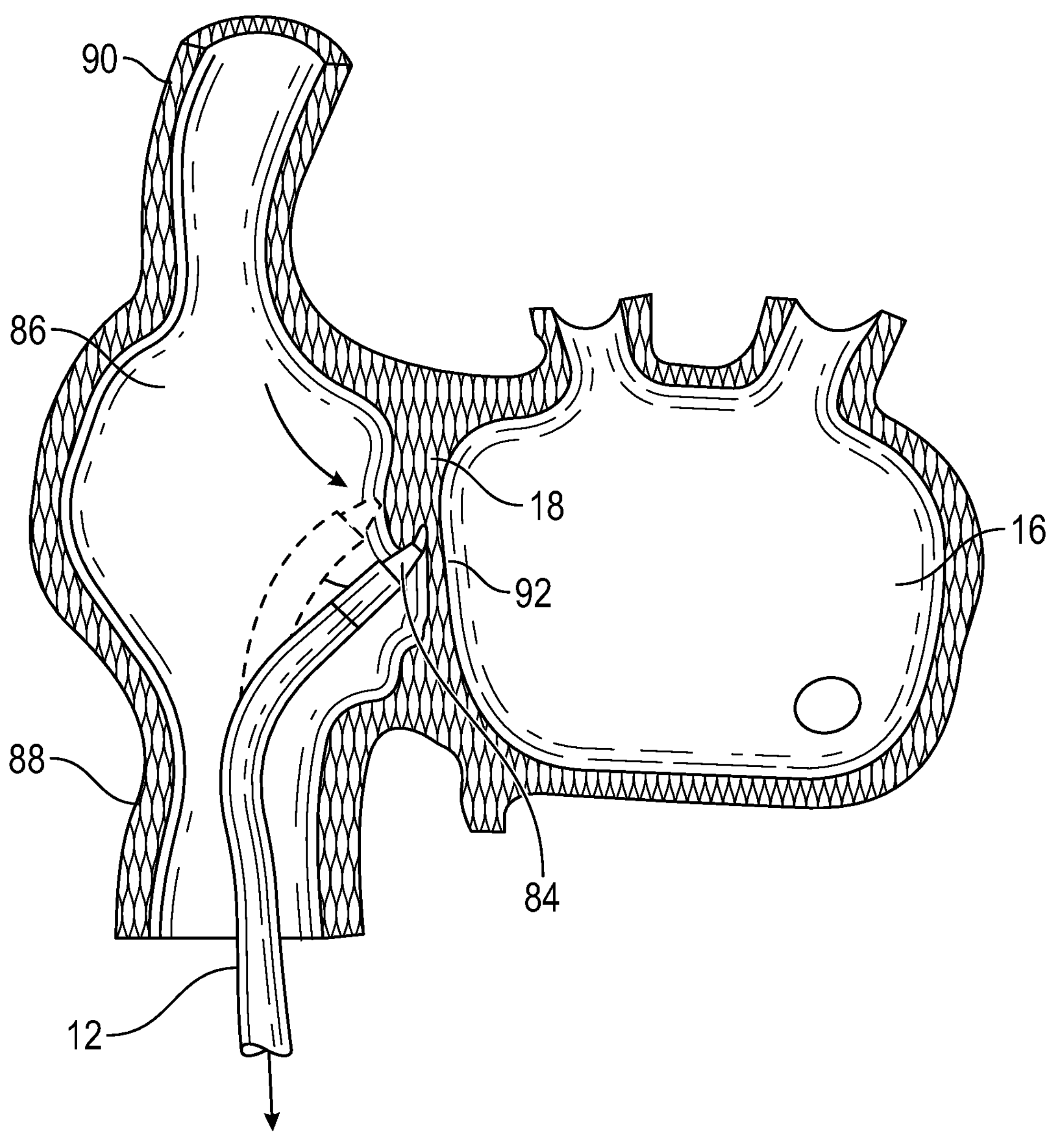
FIG. 7 is a view as in FIG. 6, showing positioning of the distal tip of the transseptal crossing system at the fossa ovalis.

The combination of the sheath 12 with the dilator 84 having the transseptal cannula 206 and GW 210 extending distally therefrom, is then drawn proximally from the superior vena cava while a curved section of the sheath, alone or in combination with a preset curve at the distal region of dilator 84 and or cannula 206, causes the tip of the cannula—GW combination to "drag" along the wall of the right atrium 86 and the septum 18, by proximal traction until the tip pops onto the fossa ovalis 92, as shown in FIG. 7.

Figure 8:
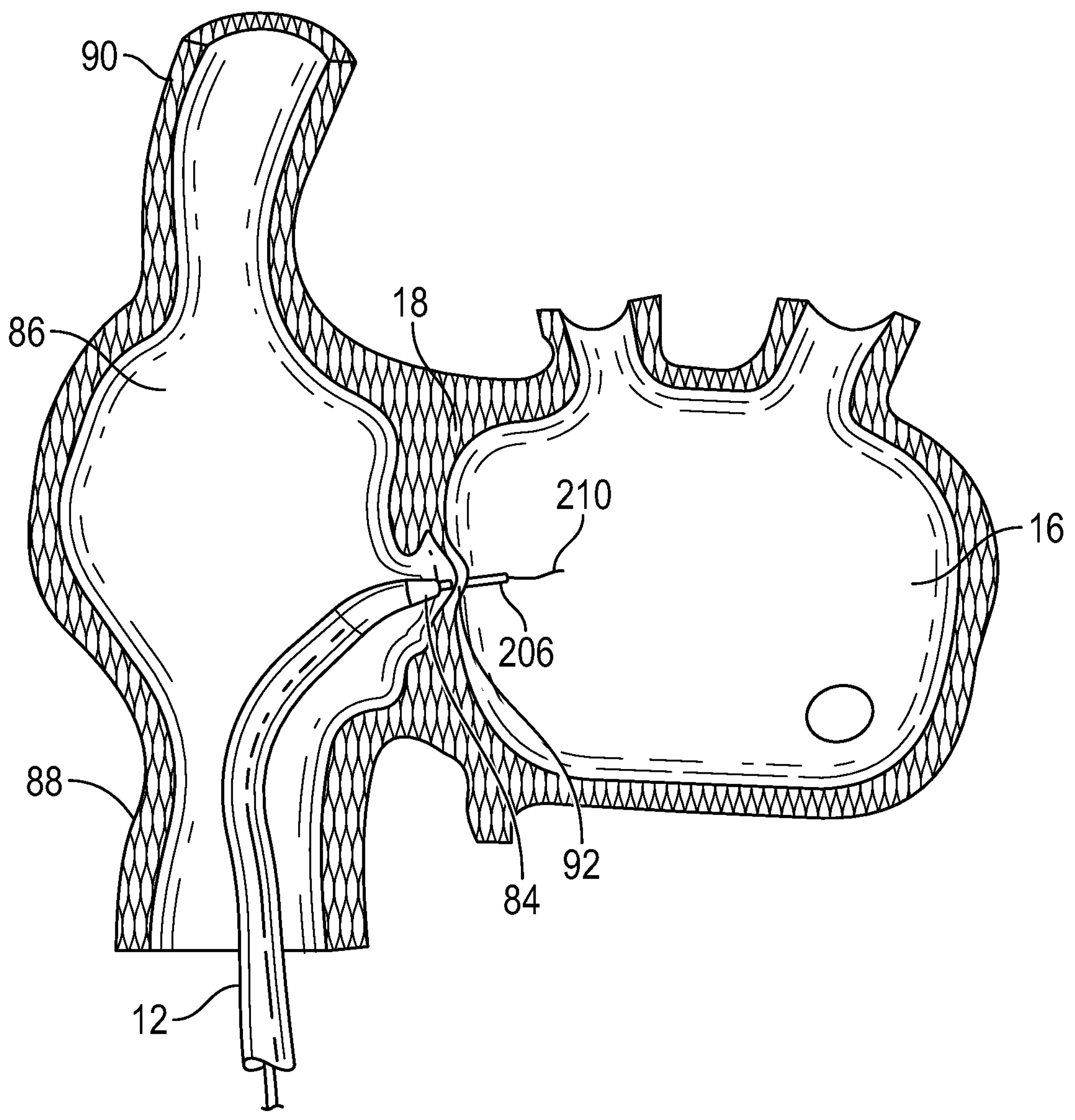
FIG. 8 shows penetration of the guidewire and cannula through the fossa ovalis.

After the tip of the cannula—GW combination has been placed in the desired location against the fossa ovalis 92, RF energy is applied via the tip of the transseptal GW 210 to allow the GW 210 to pass through the septum into the LA. As previously described, RF energy may also be delivered via the distal end of the cannula 206 if desired. See FIGS. 8 and 9.

One medical technique is to confirm the presence of the tip of the transseptal GW 210 within the left atrium 16. Confirmation of such location of the tip of the transseptal GW 210 may be accomplished by monitoring the pressure sensed through a transseptal GW lumen or an annular lumen defined between the GW 210 and the inside surface of the cannula 206 central lumen to ensure that the measured pressure is within the expected range and has a waveform configuration typical of left atrial pressure. Alternatively, proper position within the left atrium 16 may be confirmed by analysis of oxygen saturation level of the blood drawn through an available lumen; i.e., aspirating fully oxygenated blood. Finally, visualization through fluoroscopy alone, or in combination with the use of dye, may also serve to confirm the presence of the tip of the transseptal cannula 206 and GW 210 in the left atrium 16.

Figure 9:
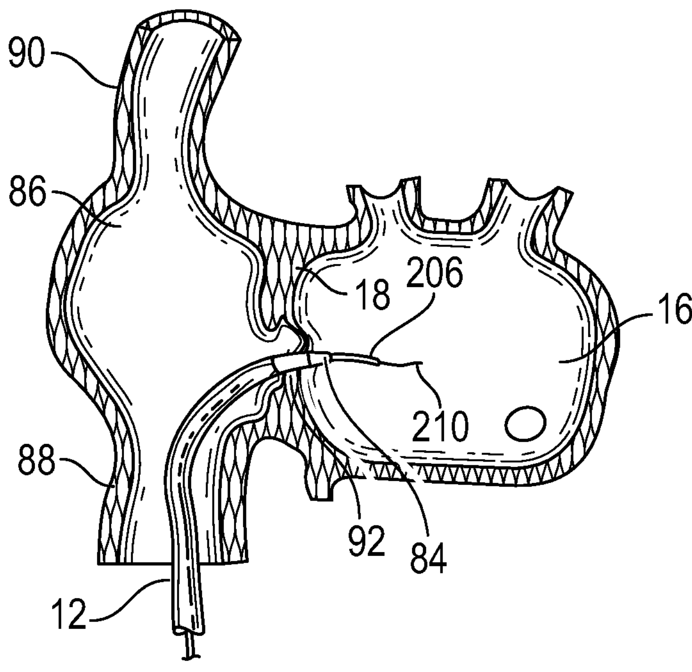
FIG. 9 shows penetration of the large bore sheath and dilator crossing the fossa ovalis.
Figure 10:
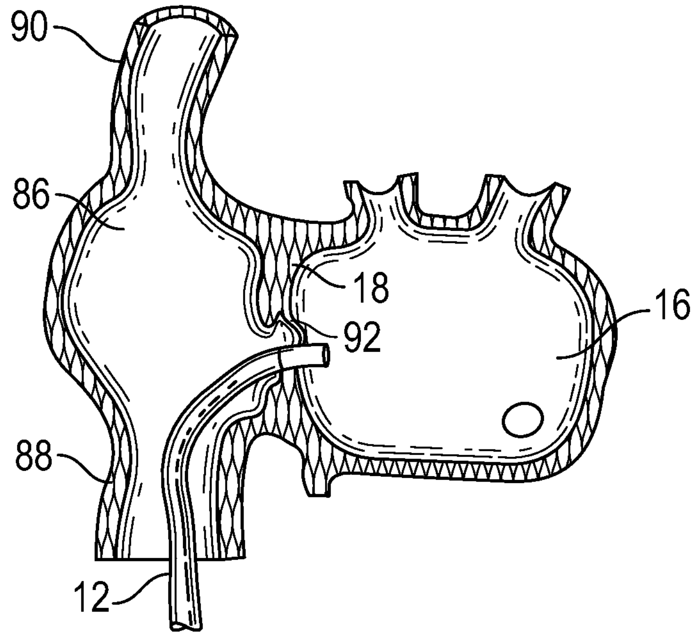
FIG. 10 shows the large bore sheath in position across the septum with the dilator and other system components removed to provide access to the left atrium.

After placing the transseptal cannula tip within the left atrium 16, the tip of the dilator 84 is advanced through the septum 18 and into the left atrium 16, as shown in FIG. 9. When the tapered tip of dilator 84 appears to have entered the left atrium 16, the transseptal cannula 206 may be withdrawn. The large bore sheath 12 may then be advanced into the left atrium 16, either by advancing the sheath 12 alone over the dilator 84 or by advancing the sheath 12 and dilator 84 in combination. The dilator 84 may then be withdrawn from sheath 12 when the latter has been advanced into the left atrium, thus leaving the main lumen of sheath 12 as a clear pathway to advancing further large bore diagnostic or therapeutic instruments into the left atrium.

What is claimed is:

1. A transseptal crossing catheter system, the system comprising:

an electrically enabled introducer sheath comprising:
- an elongate, flexible tubular body comprising an electrically conductive sidewall defining a central lumen, the electrically conductive sidewall comprising:
- a proximal end, and
- a distal end comprising an annular surface disposed on a distal-most face of the elongate, flexible tubular body, the annular surface being integral with the proximal end of the electrically conductive sidewall and being electrically conductive;
- at least four distal extensions disposed on the distal end, wherein the at least four distal extensions are configured to enhance delivered radiofrequency energy density to organic tissue, and wherein each of the at least four distal extensions comprise a leading charge transfer surface forming a scalloped surface;

a wire being movable relative to the elongate, flexible tubular body to extend at least partially through the electrically enabled introducer sheath and to extend distally through and beyond the annular surface of the elongate, flexible tubular body;

a first tubular insulation layer surrounding the electrically conductive sidewall and leaving the annular conductive surface exposed at the distal end;

a second insulation layer disposed on an outer surface of the wire, wherein the second insulation layer is separate from the first tubular insulation layer, and wherein the second insulation layer is in between the wire and the electrically conductive sidewall; and a proximal hub on the elongate, flexible tubular body comprising:

at least one access port in communication with the proximal end and the central lumen, and a connector in electrical communication with the electrically conductive sidewall.

2. The system as in claim 1, wherein the electrically conductive sidewall comprises a stainless steel tube.

3. The system as in claim 1, wherein the electrically enabled introducer sheath has an outside diameter of about 0.050 inches.

4. The system as in claim 3, wherein the electrically enabled introducer sheath has an inside diameter sufficient to receive a 0.035 inch guidewire.

5. The system as in claim 4, wherein the wire comprises a 0.035 inch guidewire having sufficient structural integrity to guide a large bore catheter transvascularly through a septal wall and into a left atrium of a heart without breaking.

6. The system as in claim 5, wherein the large bore catheter has an inside diameter sufficient to receive the electrically enabled introducer sheath therethrough.

7. The system as in claim 1, wherein the electrically enabled introducer sheath has an outside diameter of at least about 0.040 inches.

8. The system as in claim 1, wherein the electrically enabled introducer sheath has an outside diameter of at least about 0.045 inches.

9. The system as in claim 1, wherein the electrically enabled introducer sheath exhibits sufficient structural integrity to guide a large bore catheter transvascularly through a septal wall and into a left atrium of a heart without breaking.

10. The system as in claim 9, in which no part of the electrically conductive sidewall is a braided or woven wire.

11. The system as in claim 1, wherein an outer diameter of the elongate, flexible tubular body remains substantially constant from the distal end towards the proximal end.

12. The system as in claim 1, wherein an outer diameter of the proximal end of the elongate, flexible tubular body tapers towards an outer diameter of the distal end of the elongate, flexible tubular body, and wherein the outer diameter of the proximal end is greater than the outer diameter of the distal end.

13. A transseptal crossing catheter system, the system comprising:

an electrically enabled introducer sheath comprising:

an elongate, flexible tubular body comprising an electrically conductive sidewall defining a central lumen, the electrically conductive sidewall comprising:

a proximal end, a distal end comprising an annular surface disposed on a distal-most face of the elongate, flexible tubular body, the annular surface being integral with the proximal end of the electrically conductive sidewall and being electrically conductive, and at least four distal extensions disposed on the distal end, wherein the at least four distal extensions are configured to enhance delivered radiofrequency energy density to organic tissue, and wherein each of the at least four distal extensions comprise a leading charge transfer surface forming a scalloped surface;

a first tubular insulation layer surrounding the electrically conductive sidewall and leaving the annular conductive surface exposed at the distal end;

a second tubular insulation layer disposed on an inner surface of the electrically conductive sidewall; and a proximal hub on the elongate, flexible tubular body comprising:

at least one access port in communication with the proximal end and the central lumen, and a connector in electrical communication with the electrically conductive sidewall; and a wire being movable relative to the elongate, flexible tubular body to extend at least partially through the electrically enabled introducer sheath and to extend distally through and beyond the annular surface of the elongate, flexible tubular body.

14. The system of claim 13, wherein the leading charge transfer surface comprises a substantially flat surface.

15. The system of claim 13, wherein the leading charge transfer surface is configured to enhance delivered energy density.

* * * * *